(12) United States Patent
Ferrand et al.

(10) Patent No.: US 9,562,957 B2
(45) Date of Patent: Feb. 7, 2017

(54) METHOD OF PRODUCING A COMPACT CONTROL MODULE FOR A HIGH FREQUENCY ANTENNA FOR A NUCLEAR MAGNETIC RESONANCE IMAGING DEVICE

(75) Inventors: Guillaume Ferrand, Paris (FR); Michel Luong, Villeneuve Saint-Georges (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 563 days.

(21) Appl. No.: 14/233,936

(22) PCT Filed: Jul. 6, 2012

(86) PCT No.: PCT/FR2012/051602
§ 371 (c)(1),
(2), (4) Date: Apr. 3, 2014

(87) PCT Pub. No.: WO2013/011223
PCT Pub. Date: Jan. 24, 2013

(65) Prior Publication Data
US 2014/0232404 A1    Aug. 21, 2014

(30) Foreign Application Priority Data

Jul. 20, 2011 (FR) ...................... 11 56597

(51) Int. Cl.
*G01V 3/00* (2006.01)
*G01R 33/36* (2006.01)
(Continued)

(52) U.S. Cl.
CPC .............. *G01R 33/36* (2013.01); *G01R 33/34* (2013.01); *A61B 5/055* (2013.01); *G01R 33/3415* (2013.01);
(Continued)

(58) Field of Classification Search
USPC ......................................... 324/318
See application file for complete search history.

(56) References Cited

U.S. PATENT DOCUMENTS

| 4,746,866 A | 5/1988 | Roschmann |
| 4,751,464 A | 6/1988 | Bridges |
(Continued)

FOREIGN PATENT DOCUMENTS

FR    2 956 744    8/2011

OTHER PUBLICATIONS

International Search Report as issued for International Application No. PCT/FR2012/051602.
(Continued)

*Primary Examiner* — Rodney Fuller
(74) *Attorney, Agent, or Firm* — Pillsbury Winthrop Shaw Pittman LLP (57) ABSTRACT

A method of making a compact control module of a high frequency antenna for a magnetic resonance imaging device including M control elements and N radiating elements, N greater than M, the control module represented by a control matrix $\tilde{P}$, approximately equal to a control matrix P to control the radiating elements, the method including: decomposing the control matrix $\tilde{P}$ into a product of two matrices H×L; the matrix L with dimensions M×M capable of transforming M signals $V_m$ transmitted by M control elements into M signals $V_l$, in amplitude and in phase; the matrix H with dimensions N×M receiving the M signals $V_l$ as inputs; producing the matrix FI with a number of stages less than a number of stages necessary for implementation of the matrix P; and using the matrix L starting from implementation of the matrix H determined during the producing.

8 Claims, 4 Drawing Sheets

(51) Int. Cl.
*G01R 33/34* (2006.01)
*A61B 5/055* (2006.01)
*G01R 33/3415* (2006.01)
*G01R 33/561* (2006.01)

(52) U.S. Cl.
CPC ...... *G01R 33/5612* (2013.01); *Y10T 29/49016* (2015.01)

(56) References Cited

U.S. PATENT DOCUMENTS

| | | | | |
|---|---|---|---|---|
| 5,461,314 | A * | 10/1995 | Arakawa | G01R 33/3628 324/318 |
| 5,499,001 | A * | 3/1996 | Degun | H01P 5/187 333/115 |
| 5,557,247 | A | 9/1996 | Vaughn, Jr. | |
| 8,217,651 | B2 * | 7/2012 | Wiesinger | G01R 33/3621 324/309 |
| 2008/0272783 | A1 | 11/2008 | Okamoto | |
| 2009/0237077 | A1 * | 9/2009 | Vaughan | G01R 33/3415 324/307 |
| 2010/0052679 | A1 | 3/2010 | Zelinski et al. | |
| 2010/0253345 | A1 * | 10/2010 | Vester | G01R 33/3415 324/316 |
| 2010/0253346 | A1 * | 10/2010 | Hulbert | G01R 33/3415 324/316 |
| 2010/0253354 | A1 * | 10/2010 | Hulbert | G01R 33/3415 324/322 |
| 2011/0215803 | A1 * | 9/2011 | Bitz | G01R 33/5612 324/307 |
| 2013/0002254 | A1 * | 1/2013 | Ferrand | G01R 33/3415 324/322 |

OTHER PUBLICATIONS

Alagappan, V., et al., "Degenerate Mode Band-Pass Birdcage Coil for Accelerated Parallel Excitation," Magnetic Resonance in Medicine, vol. 57, May 29, 2007, pp. 1148-1158.

Setsompop, K., et al., "Slice-Selective RF Pulses for In Vivo B Inhomogeneity Mitigation at 7 Tesla Using Parallel RF Excitation With a 16-Element Coil," Magnetic Resonance in Medicine, vol. 60, No. 6, Dec. 1, 2008, pp. 1422-1432.

Pozar, D. (2005). The Quadrature (90°) Hybrid. *Microwave Engineering*. $3^{rd}$ Edition. (pp. 333-337). Hoboken, New Jersey: John Wiley & Sons, Inc.

Toker, C., et al., "Branch-Line Couplers Using Unequal Line Lengths," IEEE Transactions on Microwave Theory and Techniques, vol. 49, No. 4, Apr. 2001, pp. 718-721.

* cited by examiner

| (°) | Coupling (dB) |
|---|---|
| 0 | ∞ |
| 15 | 11.7 |
| 30 | 6.0 |
| 45 | 3.0 |
| 60 | 1.25 |
| 75 | 0.30 |
| 90 | 0 |

$$|P| = \begin{pmatrix} 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & c0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \\ 0.25 & 0.25 & 0.25 & 0.25 & 0.25 & 0.25 & 0.25 & 0.25 \end{pmatrix}$$

$$arg(P) = \begin{pmatrix} -112.5 & -135 & -112.5 & 180 & -135 & 180 & 180 & 90 \\ -135 & 180 & 180 & 90 & 112.5 & 45 & 22.5 & -90 \\ -157.5 & 135 & 112.5 & 0 & 0 & -90 & -135 & 90 \\ 180 & 90 & 45 & -90 & -112.5 & 135 & 67.5 & -90 \\ 157.5 & 45 & -22.5 & 180 & 135 & 0 & -90 & 90 \\ 135 & 0 & -90 & 90 & 22.5 & -135 & 112.5 & -90 \\ 112.5 & -45 & -157.5 & 0 & -90 & 90 & -45 & 90 \\ 90 & -90 & 135 & -90 & 157.5 & -45 & 157.5 & -90 \\ 67.5 & -135 & 67.5 & 180 & 45 & 180 & 0 & 90 \\ 45 & 180 & 0 & 90 & -67.5 & 45 & -157.5 & -90 \\ 22.5 & 135 & -67.5 & 0 & 180 & -90 & 45 & 90 \\ 0 & 90 & -135 & -90 & 67.5 & 135 & -112.5 & -90 \\ -22.5 & 45 & 157.5 & 180 & -45 & 0 & 90 & 90 \\ -45 & 0 & 90 & 90 & -157.5 & -135 & -67.5 & -90 \\ -67.5 & -45 & 22.5 & 0 & 90 & 90 & 135 & 90 \\ -90 & -90 & -45 & -90 & -22.5 & -45 & -22.5 & -90 \end{pmatrix}$$

METHOD OF PRODUCING A COMPACT CONTROL MODULE FOR A HIGH FREQUENCY ANTENNA FOR A NUCLEAR MAGNETIC RESONANCE IMAGING DEVICE

CROSS-REFERENCE TO RELATED APPLICATIONS

This application is the U.S. National Stage of PCT/FR2012/051602, filed Jul. 6, 2012, which in turn claims priority to French Application No. 1156597, filed Jul. 20, 2011. The content of both applications are incorporated herein by reference in their entirety.

This invention relates to the control of a high frequency multiple-channel antenna in reception and/or in transmission used in Nuclear Magnetic Resonance (NMR) devices and their applications; Magnetic Resonance Imaging (MRI) for men or animals, Magnetic Resonance Spectroscopy (MRS) or diffusion tensor imaging.

The field of the invention is Nuclear Magnetic Resonance (NMR) and more particularly high frequency antennas of the phased array type used in Magnetic Resonance Imaging (MRI) devices with a very high magnetic field, in other words greater than or equal to 7 Tesla.

The invention is particularly applicable to the control of a high frequency antenna of the phased array type used to examine a part of the human body, for example such as a patient's head.

Antennas of the MRI devices are formed in a known manner using radiating elements with variable shapes made of copper or a copper strips, acting either as transmitting coils in resonance with the circuit that powers it, or as relaxation signal receivers, or more generally both of these functions alternately. They surround the patient or only the part of the body to be analysed.

Placed in the permanent longitudinal magnetic field $B_0$ of an MRI device, they receive an electrical excitation by which they produce the radiofrequency (RF) magnetic field $B_1^+$ orthogonal to $B_0$ at the precession resonant frequency (also called the Larmor frequency) of the nuclei of the studied atoms that are located in the magnetic field $B_0$ and/or pick up the echo, also the radiofrequency wave at the Larmor frequency produced by atoms to which the magnetic field $B_1^+$ was temporarily applied.

Remember that magnetic spin moments of atom nuclei (for example nuclei of hydrogen atoms) will progressively align under the effect of the static magnetic field $B_0$ along a direction initially parallel to the magnetic field $B_0$ and will result in global magnetisation along the direction of the field $B_0$ called the longitudinal direction z.

When an excitation is applied in pulse form, in other words a magnetic field oscillating at the Larmor frequency denoted $B_1^+$, the magnetic spin moments will resonate and progressively separate from this longitudinal axis z describing a movement called a precession movement. Therefore the magnetic field $B_1^+$ can "tilt" the magnetic spin moments to put them in a plane perpendicular to the direction of the field $B_0$ at a tilt angle FA relative to the direction z.

When excitation is interrupted, the magnetic spin moments that separated from their initial axis return to their equilibrium position, in other words the z axis, without stopping rotating. This return to equilibrium is called relaxation. It is then possible to measure this spin rotation movement in the form of an oscillating radiofrequency signal that has the same frequency as the exciter magnetic field, in other words the Larmor resonant frequency. This signal is then picked up by the antenna switched onto the reception system comprising very low noise amplifiers or by another antenna.

One of the problems that occurs with such head antennas lies in the fact that they operate in a near electromagnetic field, unlike other antennas, in other words the physical radiating elements are placed close to the sample (i.e. the patient's head).

Conventionally, intensities of the magnetic field $B_0$ used in medical imaging are between 0.1 and 3 Tesla.

At these low magnetic field intensities, the operating frequency corresponding to the Larmor frequency remains low. For example, for a magnetic field $B_0$ of 1.5 Tesla, the corresponding Larmor frequency is 64 MHz and the Larmor frequency corresponding to a magnetic field $B_0$ of 3 Tesla is 128 MHz.

In general, the antennas used to examine the head at low field (between 0.1 and 3 Tesla) are so-called 3-D antennas of the bird cage or TEM (Traverse Electric and Magnetic) type as described in documents U.S. Pat. No. 4,746,866, U.S. Pat. No. 4,751,464, U.S. Pat. No. 5,557,247. These bird cage type antennas are optimised to produce the highest magnetic field with the least power.

These bird cage type antennas comprise a set of coupled radiating elements and are powered by a single channel, in other words a single power inlet creating a rotating magnetic field, the power inlet itself being powered by a single control element.

This type of antenna can give satisfactory results and particularly a relatively uniform magnetic field $B_1^+$ over the entire zone to be studied at magnetic field intensities referred to as low and medium magnetic field intensities. With low applied magnetic fields, in other words up to 3 Tesla, the corresponding Larmor frequency remains low and artefacts called B1 or RF (radiofrequency) are tolerable.

However, the intensity of the magnetic field $B_0$ of the static magnet is tending to increase due to the drive to improve the resolution of images. Thus, the bird cage type antennas become critical for high intensities of the magnetic field $B_0$, in other words greater than or equal to 7 Tesla. The oscillating frequency of the magnetic field $B_1$ that must match the Larmor frequency that is proportional to the intensity of the longitudinal static magnetic field $B_0$ then becomes greater than 298 MHz for the proton and the effective wavelength of the magnetic field $B_1$ is relatively short, of the order of a few tens of centimeters, in other words the same order of magnitude as the size of the sample to be studied, particularly, the patient's head.

Furthermore, much of the electromagnetic power within this frequency range is lost in the sample, particularly around the periphery of the sample that means that areas at a distance from the periphery of the sample receive less power. In this frequency range, electromagnetic waves are also irregular in shape creating local concentrations of the magnetic field at the centre of the sample.

Antennas of the phased array type formed by a combination of a plurality of surface antennas also called radiating elements have been developed to overcome this problem of non-uniformity of the magnetic field denoted by the artefact B1 or RF, in which each surface antenna comprises a specific channel for transmission and reception of the signal. Each surface antenna can thus produce an image of the anatomic region facing which it is located, the different images are then combined by algorithms to form the final image. It has also been demonstrated that excitation of protons is made more uniform when the number of radiating elements of an antenna increases.

In current operating configurations of these phased array type antennas, each channel of the antenna should be connected to a power amplifier and each power amplifier is controlled independently with an amplitude and a particular phase shift through a man/machine interface.

The disadvantage of this technology is the high cost of production that is due particularly to the large number of power amplifiers and especially to the control electronics (control of the amplitude and control of the phase shift) necessary to control each channel of the antenna. Thus, a specific control system is assigned to each channel of the antenna.

Control processes have been developed to reduce production costs of a array antenna that consist of constructing the N signals $V_a$ (M<N) that will be used on the N radiating elements, starting from M signals $V_m$ output from M control systems with an appropriate amplitude and phase. Matching between the M signals generated by the M control systems and the N signals to be used by the N radiating elements is obtained by a calculation expressed below, and that it is convenient to express in matrix form. There is thus a matrix P called the control matrix, such that the matrix of the various signals $V_a$ is deduced from the signals matrix $V_m$ by multiplying it by the control matrix P that generally has complex coefficients:

$$V_a = P V_m$$

Figure 1:
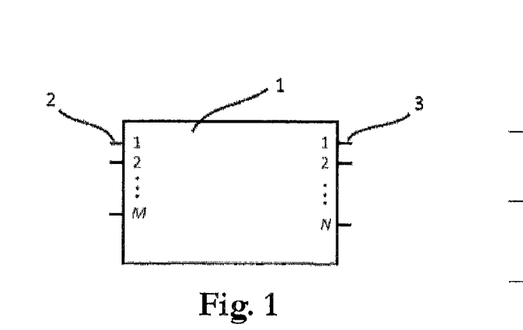
FIG. 1 shows a diagrammatic representation of the inputs and outputs of a control module representing a modal control matrix P for control of a high frequency antenna, of the phased array type.

FIG. 1 shows a diagrammatic view of inputs 2 and outputs 3 associated with a control module 1 representing a modal control matrix with M modes (inputs) for N radiating elements (outputs) where M<N.

Up to now, these control module production methods have been based on the decomposition of all possible excitation combinations on an orthogonal base of N modes (where N represents the number of radiating elements distributed around a cylindrical shell forming the antenna). This decomposition advantageously shows that the number of actually efficient modes is less than the number N of radiating elements.

It is known that excitation combinations can be decomposed into N orthogonal modes according to two methods of converting signals, such that a control system generating an input signal 2 associates a signal with the same amplitude or a different amplitude at several outputs 3, for which the phase varies depending on the propagation mode to be excited.

A first method consists of using a Butler matrix like that mentioned in article "Slice-Selective RF pulses for in vivo B1 inhomogeneity mitigation at 7 Tesla using parallel RF excitation with a 16-element coil", 2008, Kawin Setsompop and in article "Degenerate mode bandpass birdcage coil for accelerated parallel excitation", 2007, Alagappan V. et al.

A second method consists of making a Singular Value Decomposition (SVD). In general the SVD method is preferable to the decomposition using the Butler's matrix because it can take account of the interaction of the antenna with the sample (for example the human head) and can order modes to be excited in order of efficiency. This singular value decomposition method applied to the control of a array antenna is disclosed in particular in patent application FR10/0072907.

Regardless of what method is used, a number M of excitation modes around N/2 is sufficient to obtain a satisfactory result in parallel transmission. Note that strict orthogonality of selected modes is not essential.

In practice the modal control matrix, subsequently called the P matrix, resulting from the decomposition (by Butler matrix or SVD) is physically constructed through the assembly of several couplers and/or several signal phase shifters.

Thus for example for an antenna comprising 16 radiating elements, the control matrix P obtained by use of the Butler matrix is produced by 4 successive stages each composed of 8 hybrid couplers.

Note that stage means the physical composition of three elements formed by hybrid couplers, phase shift line and line permutations. Therefore one stage is sufficient to distribute N input signals onto N different output signals with a phase shift and a permutation specific to each signal.

Considering the structure of hybrid couplers comprising two inputs and two outputs, the maximum number of channels or radiating elements N that can be excited by a control system for K stage(s) is given by the following relation:

$$\max N = 2^k$$

Conversely, if the antenna has N radiating elements, it is necessary that the number of channels that can be excited by the control system is greater than the number of radiating elements N. Consequently, it is necessary that:

$$N \leq 2^k$$

Let $E_{SUP}(N)$ denote the "excess" integer part of N, in other words the nearest integer greater than or equal to N, the number of stages K obtained must be greater than or equal to:

$$E_{SUP}(\ln(N)/\ln(2))$$

where
N is the number of radiating elements;
"ln" is the Naperian logarithm.

For example, for an antenna comprising 16 radiating elements, the Butler matrix requires a control module comprising 4 stages of 8 couplers, and the more efficient SVD matrix requires a control module comprising 8 stages of 8 couplers.

Although physically possible, these control matrices P (Butler matrix or SVD matrix) are complex to manufacture, have a relatively high cost and a non-negligible insertion loss, in other words non negligible attenuation of the signal power between the input and the output (in dB).

This is the context in which this invention aims to solve the problems mentioned above by disclosing a method of making a control module for a high frequency phased array type antenna capable of minimising costs and the complexity of making such a control module while having sufficient quality and precision for a Magnetic Resonance Imaging application.

To achieve this, the invention discloses a method of making a compact control module of a high frequency antenna for a magnetic resonance imaging device comprising a plurality M of control elements and a plurality N of radiating elements, said plurality N of radiating elements being greater than said plurality M of control elements, said control module being represented by a control matrix $\tilde{P}$, where $\tilde{P}$ is a matrix approximately equal to the control matrix P to control said plurality N of radiating elements using said plurality M of control elements; said method comprising:
- a step to decompose the approximate control matrix $\tilde{P}$ into a product of two matrices H×L; the first matrix L with dimensions M×M being capable of transforming a plurality M of signals V, transmitted by said plurality M of control elements into M signals $V_l$ in amplitude and in phase; the second matrix H with dimensions N×M receiving said M signals $V_l$ as inputs;

a step to produce said matrix H with a number of stages less than the number of stages necessary for implementation of the control matrix P, said stages being implemented by coupling means, phase shifting means and permutation means;

a step to use said matrix L by software means starting from implementation of said matrix H determined during the previous step.

The invention consists of disclosing an advantageous decomposition of a matrix $\tilde{P}$ approximating a control matrix P of the Butler matrix or SVD matrix type, in the form of a product of two distinct matrices, a first matrix L and a second matrix H, and using the matrix L in digital form by software means, in order to thus reduce the complexity of the physical production of the control matrix P by implementation of the simplified matrix H.

Additional degrees of freedom and/or the various possible combinations of signals that can be made by digital implementation of the matrix L can define a simple matrix H and particularly with a smaller number of stages, advantageously with a number of stages less than the number of stages for implementation of the control matrix P without the advantageous decomposition according to the invention.

The number of stages K necessary to implement the matrix H is typically less than the relation $E_{sup}(\ln(N)/\ln(2))$.

Thus, for an example of an antenna comprising 16 radiating elements and 8 inputs or relevant modes to be synthesised, the invention reduces the number of stages from 4 to 2 for a so-called Butler matrix configuration and from 8 to 3 for a so-called SVD matrix configuration.

Advantageously, a single hybrid coupler is used in these example embodiments. This hybrid coupler is characterised by a 6-decibel (dB) distribution of the power from one input to the two outputs with a phase shift of 90°.

The method according to the invention can thus result in a large improvement in robustness, cost and insertion loss for the control matrix, compared with the state of the art.

The method according to the invention can also have one or several of the above characteristics considered individually and in any technically possible combination:

said implemented matrix H comprises a number of stages K less than:

$E_{sup}(\ln(N)/\ln(2))$, where $E_{sup}$ corresponds to the next higher integer part
N corresponds to the number of radiating elements of the antenna;
"ln" corresponds to the Naperian logarithm.
the method includes a step to decompose the matrix H into a plurality K+1 of matrices S according to the following relation:

$H = S_K S_{k-1}, \ldots, S_1 S_0$ where $S_0$ is a matrix with dimensions N×M
$S_k$ is a matrix with dimensions N×N where $k=\{1, \ldots, K\}$
each of said matrices $S_k$ where $k=\{1, \ldots, K\}$ is formed by the matrix product of a coupling matrix $C_k$, a phase shift matrix $\Phi_k$ and a permutation matrix $\Pi_k$ such that a signal $X_{k+1}$ at the output from stage k of the control module depends on the relation:

$X_{k+1} = S_k X_k = \Pi_k \Phi_k C_k X_k$, where $X_k$ represents the input signal to said stage k;
said coupling matrix $C_k$ is implemented by said coupling means, said phase shift matrix $\Phi_k$ is implemented by said phase shift means, and said permutation matrix $\Pi_k$ is implemented by permutation means;

said coupling means are universal hybrid couplers;
said coupling means are universal 6 dB hybrid couplers;

Another purpose of the invention is a control module obtained by the manufacturing method according to the invention, characterised in that it comprises an arrangement of coupling means, phase shift means and permutation means and software means such that a signal $V_a$ output from said control module depends on the relation:

$V_a = HLV_m$ where $V_m$ represents the M input signals to said control module;
H is the matrix with dimensions N×M that can be implemented by said coupling means, said phase shift means and said permutation means;
L is the matrix with dimensions M×M that can be used by said software means.

Other characteristics and advantages of the invention will become clearer after reading the following description given for information and in no way limitative, with reference to the appended figures among which.

Common elements have the same reference numbers in all the figures.

FIG. 1 has already been described with reference to the presentation of the state of the art.

The method according to the invention can be used to make a control module capable of controlling a phased network antenna with fewer control elements than radiating elements of the antenna (i.e. N>M).

The term "control element" is used to refer to an electronic sub-set usually comprising a fast amplitude modulator and a fast phase modulator controlled by the computer system of the MRI device and accessible to the operator through a man-machine interface.

Consider a control matrix P usually with complex values, with dimensions N×M, used to transform an input variable denoted $V_m$ representing the voltage applied at the input ports of the control matrix P and associated with each of the M modes, and an output variable denoted $V_a$ representing the voltage seen at the output ports, associated with each of the N radiating elements of the network antenna.

Thus the control matrix P transforms $V_m$ into $V_a$ using the matrix product:

$V_a = P \cdot V_m$

The method according to the invention can be used to implement an approximate control matrix $\tilde{P}$, that can be produced easily while minimising the error $\epsilon$ defined by the relation:

$$\epsilon = \|(\tilde{P}-P)W\|$$

where:

$\|\square\|$ denotes the Euclidean norm

W denotes a diagonal matrix with dimensions M×M, the coefficients of which define the weight of each mode in the error calculation.

The accepted error for the mode i considered reduces as the size of the elements W(i,i) of the matrix W increases. The use of the matrix W can thus minimise the error for some modes (i.e. the most important modes) while giving more freedom to other modes.

Implementation of the approximate control matrix is decomposed into two parts or two blocks:
- a first physical block subsequently called the compact distributor and that is associated with a reduced matrix called the matrix H;
- a second block called the virtual block associated with a virtual matrix called the matrix L and that is implemented by software means.

The dimensions of the reduced matrix H are N×M and the dimensions of the virtual matrix L are M×M.

An output variable denoted $V_l$ (column matrix) is associated with the virtual matrix L and is defined by the relation:

$$V_l = L \cdot V_m$$

In other words, if the user would like to excite a mode m, all that is necessary is that the software means calculate signals associated with the variable $V_l$ and apply them on the inputs to the compact distributor characterised by the reduced matrix H.

If production of the compact distributor has to satisfy physical feasibility constraints, the virtual device representing the virtual matrix is free of all constraints. Thus, the method according to the invention can optimise a control matrix P by the product of two matrices, one of which is a reduced matrix H that can be easily and simply produced through the choice of hybrid couplers and preferably by universal hybrid couplers so as to reduce the production costs of such a control module.

The matrix H is implemented or produced using a distribution interface followed by a number of sub-sets with a similar structure called stages. A matrix $S_k$ is associated with each of these stages with index K (k≠0). The matrix $S_k$ can transform an input variable $X_k$ into an output variable $X_{k+1}$.

The distribution interface is defined by a matrix $S_0$ with dimensions N×M because it can be used to connect the M inputs to the N outputs.

The other matrices $S_k$ are square matrices with N inputs and N outputs.

The first variable $X_0$ corresponds to the input to the compact distributor, in other words the variable $V_l$ and the last variable corresponds to the output signals capable of controlling the antenna, in other words the variable $V_a$.

Thus, if the number of stages is equal to K then the following matrix expression is valid:

$$V_a = S_k S_{k-1} \ldots S_1 S_0 V_l$$

The matrix $S_0$ provides a connection between the M inputs and N outputs without modifying the signals. Physically, this first distribution interface 11, an example representation of which is given in FIG. 2, may comprise direct connections and adapted loads (50Ω, equal to the characteristic impedance of transmission lines). Thus, elements of the matrix $S_0$ are written simply as follows: $S_0(i,j)=1$ if input i is connected directly to input j, otherwise the element is equal to zero.

Figure 2:
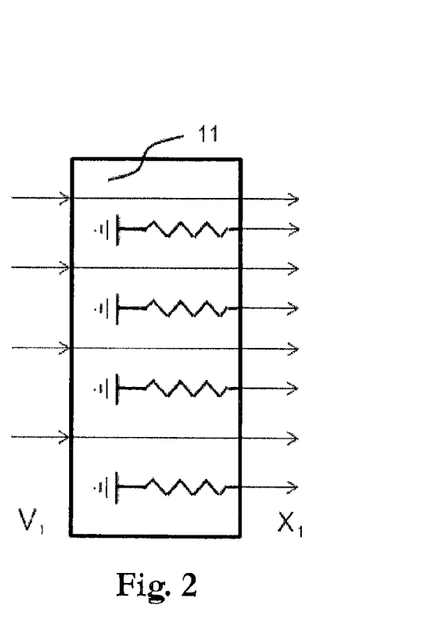
FIG. 2 shows an example embodiment of a control module distribution interface shown in FIG. 1.

Thus for example, for 8 inputs to 16 outputs, $S_0$ can be in the following form:

$$S_0 = \begin{pmatrix} 1 & 0 & 0 & 0 & 0 & 0 & 0 & 0 \\ 0 & 0 & 0 & 0 & 0 & 0 & 0 & 0 \\ 0 & 1 & 0 & 0 & 0 & 0 & 0 & 0 \\ 0 & 0 & 0 & 0 & 0 & 0 & 0 & 0 \\ 0 & 0 & 1 & 0 & 0 & 0 & 0 & 0 \\ 0 & 0 & 0 & 0 & 0 & 0 & 0 & 0 \\ 0 & 0 & 0 & 1 & 0 & 0 & 0 & 0 \\ 0 & 0 & 0 & 0 & 0 & 0 & 0 & 0 \\ 0 & 0 & 0 & 0 & 1 & 0 & 0 & 0 \\ 0 & 0 & 0 & 0 & 0 & 0 & 0 & 0 \\ 0 & 0 & 0 & 0 & 0 & 1 & 0 & 0 \\ 0 & 0 & 0 & 0 & 0 & 0 & 0 & 0 \\ 0 & 0 & 0 & 0 & 0 & 0 & 1 & 0 \\ 0 & 0 & 0 & 0 & 0 & 0 & 0 & 0 \\ 0 & 0 & 0 & 0 & 0 & 0 & 0 & 1 \\ 0 & 0 & 0 & 0 & 0 & 0 & 0 & 0 \end{pmatrix}$$

It will be noted that each line in the matrix $S_0$ may comprise only one single element equal to 1 because each input can only be connected to one output.

The other subsets called stages are represented by matrices $S_k$ with dimensions N×N for k∈{1, ..., E}.

For example, for 3 stages (i.e. K=3), the matrix H may be written in matrix form with the following relation: $H = S_3 S_2 S_1 S_0$.

The matrices $S_k$ representing the stages are themselves broken down into three parts: a coupling matrix $C_k$, a phase shift matrix $\Phi_k$ and a permutation matrix $\Pi_k$.

Figure 3:
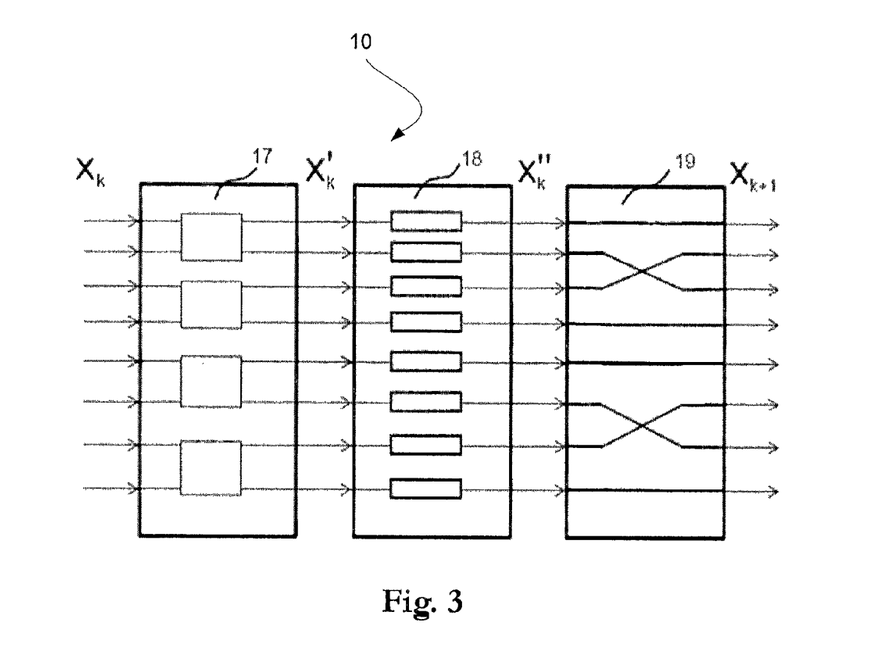
FIG. 3 shows an example embodiment of a complete stage of the control module shown in FIG. 1.

FIG. 3 gives the physical representation of a complete stage k representing a matrix $S_k$ of the previously described compact distributor. The outputs from the coupling matrix $C_k$ and the phase shift matrix $\Phi_k$ are denoted $X_k'$ and $X_k^*$ respectively.

The coupling matrices $C_k$ are materialised essentially by a combination of hybrid couplers 17, for example of the "branch-line" type ([10] "Microwave Engineering", Wiley, N.Y. 1998; Pozar, a).

Advantageously, we will define a hybrid coupler as a universal coupler characterised by a single parameter θ. Each universal hybrid 17 comprises two inputs ($e_1 e_2$) and two outputs ($\sigma_1 \sigma_2$) connected by the following matrix transformation:

$$\begin{pmatrix} \sigma_1 \\ \sigma_2 \end{pmatrix} = \begin{pmatrix} -j\cos\theta & -\sin\theta \\ -\sin\theta & -j\cos\theta \end{pmatrix} \begin{pmatrix} e_1 \\ e_2 \end{pmatrix},$$

where θ is a free parameter in the design of a hybrid coupler and that determines coupling often expressed in dB between the second output ($\sigma_2$) and the first input ($e_1$). In other words, the parameter θ defines the manner in which power is distributed on the two outputs.

Figure 4:
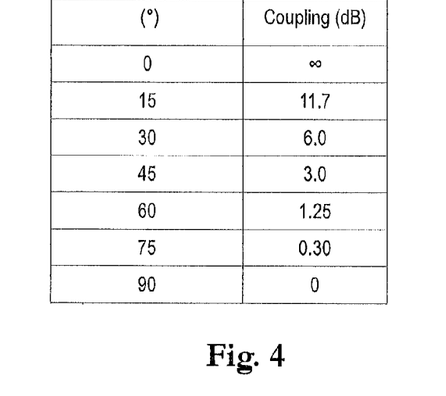
FIG. 4 is a table showing correlations between the angle parameter θ and coupling in dB.

The table shown in FIG. 4 gives different values of the angle θ for different coupling values in dB;

N/2 hybrid couplers 17 will then be used for the construction of a stage of an antenna comprising N radiating elements, where N is an even number. The inputs $X_k$ and the outputs $X'_k$ of matrix $C_k$ are then related by the following relations:

$$X'_k(2i-1) = -j\cos\theta_{k,i} X_k(2i-1) - \sin\theta_{k,i} X_k(2i),$$

$$X'_k(2i) = -\sin\theta_{k,i} X_k(2i-1) - j\cos\theta_{k,i} X_k(2i),$$

$$\text{for } i \in \left\{1, \ldots, \frac{N}{2}\right\}.$$

On the other hand, if the number N of radiating elements of the antenna is odd, (N−1)/2 universal hybrid couplers will be used that will be connected as previously but for $$\left\{1, \ldots, \frac{N}{2}\right\}.$$

Thus, the final element of the input is directly connected to the output, in other words $X'_k(N)=X_k(N)$.

With the previous notations, if the number N of radiating elements is even, the coupling matrices $C_k$ are in the form of a band matrix (non null elements are all grouped around the diagonal):

$$C_k = \begin{pmatrix} -j\cos\theta_{k,1} & -\sin\theta_{k,1} & 0 & 0 & \cdots & 0 & 0 \\ -\sin\theta_{k,1} & -j\cos\theta_{k,1} & 0 & 0 & \cdots & 0 & 0 \\ 0 & 0 & -j\cos\theta_{k,2} & -\sin\theta_{k,2} & \cdots & 0 & 0 \\ 0 & 0 & -\sin\theta_{k,2} & -j\cos\theta_{k,2} & \cdots & 0 & 0 \\ \vdots & \vdots & \vdots & \vdots & \ddots & \vdots & \vdots \\ 0 & 0 & 0 & 0 & \cdots & -j\cos\theta_{k,N/2} & -\sin\theta_{k,N/2} \\ 0 & 0 & 0 & 0 & \cdots & -\sin\theta_{k,N/2} & -j\cos\theta_{k,N/2} \end{pmatrix}$$

If the number N of radiating elements is odd, then the matrices $C_k$ will be of the following form:

$$C_k = \begin{pmatrix} -j\cos\theta_{k,1} & -\sin\theta_{k,1} & 0 & 0 & \cdots & 0 & 0 & 0 \\ -\sin\theta_{k,1} & -j\cos\theta_{k,1} & 0 & 0 & \cdots & 0 & 0 & 0 \\ 0 & 0 & -j\cos\theta_{k,2} & -\sin\theta_{k,2} & \cdots & 0 & 0 & 0 \\ 0 & 0 & -\sin\theta_{k,2} & -j\cos\theta_{k,2} & \cdots & 0 & 0 & 0 \\ \vdots & \vdots & \vdots & \vdots & \ddots & \vdots & \vdots & \vdots \\ 0 & 0 & 0 & 0 & \cdots & -j\cos\theta_{k,N'} & -\sin\theta_{k,N'} & 0 \\ 0 & 0 & 0 & 0 & \cdots & -\sin\theta_{k,N'} & -j\cos\theta_{k,N'} & 0 \\ 0 & 0 & 0 & 0 & \cdots & 0 & 0 & 1 \end{pmatrix}$$

where N'=(N−1)/2.

The phase shift produced by the phase shift matrix $\Phi_k$ consists of adding a transmission line 18 at each output from the hybrid couplers 17. Depending on their length, the transmission lines 18 modify the phase of the signal between the input $X'_k$ and the output $X''_k$ using the following relation:

$$X''_k(i) = X'_k(i) e^{j\phi_{k,i}},$$

where $\phi_{k,i} = -\beta \Delta l_{k,i} + 2\pi n$ in which:
β is the transmission line propagation constant,
$\Delta l_{k,i}$ is its physical length, and,
n is an integer number.

In matrix notation, the phase shift matrices $\Phi_k$ are written in the following form:

$$\phi_k = \begin{pmatrix} e^{j\varphi_{k,1}} & 0 & \cdots & 0 \\ 0 & e^{j\varphi_{k,2}} & \cdots & 0 \\ \vdots & \vdots & \ddots & \vdots \\ 0 & 0 & \cdots & e^{j\varphi_{k,N}} \end{pmatrix}$$

The permutation matrix $\Pi_k$ consists of connecting the inputs $X''_k$ to the outputs $X_{k+1}$, permuting their order. The operation is similar to the operation done by the distribution interface $S_0$, except that in this case the number of inputs $X''_k$ is equal to the number of outputs $X_{k+1}$.

In this case, the connections can be represented more simply by a permutation $p_k$ of the set $\{1, \ldots, N\}$ written as follows:

$$p_k = (p_k(1), p_k(2), \ldots, p_k(k))$$

in other words, the first input is connected to output $P_k(1)$, the second input is connected to output $P_k(2)$ and so on. A mathematical permutation matrix $\Pi_k$ is associated with this permutation, each element of which is defined as follows:

$$\Pi_k(i,j) = \begin{cases} 1 & \text{if } i = p_k(j) \\ 0 & \text{else} \end{cases}$$

Thus for example, if $p_k=(1,3,4,2)$ then the matrix is written as follows:

$$\Pi_k = \begin{pmatrix} 1 & 0 & 0 & 0 \\ 0 & 0 & 1 & 0 \\ 0 & 0 & 0 & 1 \\ 0 & 1 & 0 & 0 \end{pmatrix}$$

Therefore each stage can be represented by the following global matrix relation:

$$X_{k+1} = S_k X_k = \Pi_k \Phi_k C_k X_k,$$

Some of the elements described above are fixed, for example the permutations $p_k$ and the connections represented by the matrix $S_0$ and other elements may be optimised, these are the $\theta_{k,i}$ and $\phi_{k,i}$ parameters.

Therefore, permutations and connections represented by the matrix $S_0$ are chosen so as to facilitate optimisation of the $\theta_{k,i}$ and $\phi_{k,i}$ parameters.

In particular, it will be seen that if the matrix $S_0$ is badly chosen, some couplers of the first stage $C_1$ can have two inputs connected to the adapted load, and therefore become useless in the optimisation (since there is no input signal, there will be no output signal). We have advantageously chosen to define the matrix $S_0$ as follows, in order to get a better distribution of inputs relative to outputs:

$$S_k(i,j) = \begin{cases} 1 & \text{if } \mu(j) = i \\ 0 & \text{else} \end{cases}$$

where $$\mu(j) = E\left(\frac{(j-1)N}{M}\right) + 1,$$

where, in which E is the integer part.

For example, for N=16 and M=8, N/M=2 and the previously presented matrix $S_0$ is obtained, namely:

$$S_0 = \begin{pmatrix} 1 & 0 & 0 & 0 & 0 & 0 & 0 & 0 \\ 0 & 0 & 0 & 0 & 0 & 0 & 0 & 0 \\ 0 & 1 & 0 & 0 & 0 & 0 & 0 & 0 \\ 0 & 0 & 0 & 0 & 0 & 0 & 0 & 0 \\ 0 & 0 & 1 & 0 & 0 & 0 & 0 & 0 \\ 0 & 0 & 0 & 0 & 0 & 0 & 0 & 0 \\ 0 & 0 & 0 & 1 & 0 & 0 & 0 & 0 \\ 0 & 0 & 0 & 0 & 0 & 0 & 0 & 0 \\ 0 & 0 & 0 & 0 & 1 & 0 & 0 & 0 \\ 0 & 0 & 0 & 0 & 0 & 0 & 0 & 0 \\ 0 & 0 & 0 & 0 & 0 & 1 & 0 & 0 \\ 0 & 0 & 0 & 0 & 0 & 0 & 0 & 0 \\ 0 & 0 & 0 & 0 & 0 & 0 & 1 & 0 \\ 0 & 0 & 0 & 0 & 0 & 0 & 0 & 0 \\ 0 & 0 & 0 & 0 & 0 & 0 & 0 & 1 \\ 0 & 0 & 0 & 0 & 0 & 0 & 0 & 0 \end{pmatrix}$$

The permutations $P_k$ are chosen using a more heuristic approach. The permutations $p_k$ may be defined differently depending on the number of radiating elements N.

For example, for N=16 and for 3 stages, the following permutations can be chosen:
$p_1 = p_3 = (1, 3, 2, 4, 5, 7, 6, 8, 9, 11, 10, 12, 13, 15, 14, 16)$
and $p_2 = (1, 5, 2, 6, 3, 7, 4, 8, 5, 9, 13, 10, 14, 11, 15, 12, 16)$ About ten tests are usually sufficient to find the best permutations $p_k$ depending on the value of N and the number of stages required.

Since the matrix L is free, all its complex coefficients can be optimised. Thus, for N=16 radiating elements, M=8 modes and for two stages, the number of parameters to be optimised is equal to 48 unknowns with real values $\phi_{k,i}$ (32 unknowns, 16 per stage) and $\theta_{k,i}$ (16 unknowns, 8 per stage), to which 64 unknowns with complex values are added for the coefficients of the matrix L.

The optimisation algorithm uses 3 nested routines: $f_p$, $f_{nl}$, $f_{lin}$.

The linear optimisation routine $f_{lin}$ takes a matrix H as its argument and returns the matrix L that minimises the error: $\epsilon = \|P - HL)W\|$. Therefore it can be used to determine the matrix L starting from a given implementation of the matrix H. The optimisation is said to be linear and it can be demonstrated (by a so-called QR decomposition) that there is a single solution. Therefore the routine provides the matrix L and the error $\epsilon$.

The non-linear optimisation routine $f_{nl}$ uses an estimated combination of $\theta_{k,i}$ and $\phi_{k,i}$ as its argument. This routine uses a non-linear type optimisation like a Gauss-Newton optimisation. A matrix H like that describes above is associated with each combination. This optimisation searches for a combination of $\theta_{k,i}$ and $\phi_{k,i}$ such that $f_{lin}(H)$ returns a minimum local error $\epsilon$. This routine returns an optimum combination of $\theta_{k,i}$ and $\phi_{k,i}$, the matrix L and the minimum error $\epsilon$.

The main routine $f_p$ does not have an argument. It draws a random combination $\theta_{k,i}$ and $\phi_{k,i}$ and sends it the routine $f_{nl}$. A large number of combinations are chosen at random. This routine $f_p$ explores a large number of local minima. The smallest of the minima will be chosen as the final solution to the problem.

Therefore, the complete process described can be used to obtain the control matrix $\hat{P}$ that is closest to the control matrix P given at the beginning. All routines may be encoded in the Matlab calculation environment or any other environment.

Production of the compact distributor requires universal hybrid couplers 17 for each stage (FIG. 3). Each of the couplers is characterised by a single parameter, its coupling angle denoted $\theta_{k,i}$ in which i denotes the number of the coupler in stage k. The value of coupling $C_{k,i}$ in dB is defined by:

$$C_{k,i} = -20 \log_{10}|\sin \theta_{k,i}|.$$

Advantageously, the compact distributor is produced from a single type of hybrid coupler, for example with coupling of 6 dB. This 6 dB coupling means that 25% of the input power (input 1) passes through the coupled channel (output 2). According to another embodiment, each universal hybrid with angle θ may be synthesised individually based on a hybrid coupler of the "branch-line" type ([11] "Branch-line Couplers Using Unequal Line Lengths", IEEE Transactions on MTT, vol. 49, No. 4, 2001, Toker, C. et al.). However, this embodiment would require a large effort and extra cost in producing the control module because a large number of different "branch-line" couplers would be necessary. The method according to the invention can be used to make a control module with only a single "branch-line" type of coupler.

Furthermore, use of the same type of universal hybrid with a given value θ makes it easy to generate a range of universal hybrids with different values of θ, by shifting the phase and permutation of inputs and outputs.

In particular, with a 6 dB "branch-line" hybrid coupler corresponding to the universal hybrid with angle θ=30°, universal hybrids with angle θ∈{30°, 60°, 120°, 150°, 210°, 240°, 300°, 330°} can be made by shifting the phase and permutation of inputs and outputs. If we add hybrids with angle θ∈{0°, 90°, 180°, 270°} to this range of hybrids, we obtain a space of discrete solutions for universal hybrids.

Solutions of the optimisation algorithm can then be rounded to these discrete values. It is found that the last four hybrids ($\theta \in \{0°, 90°, 180°, 270°\}$) simply correspond to direct or cross connections with a phase shift:

- $\theta=0°$ corresponds to a direct connection (input $e_1$ to output $s_1$, and input $e_2$ to output $s_2$) with a phase shift of $-90°$,
- $\theta=90°$ corresponds to a cross connection (input $e_1$ to output $s_2$, and input $e_2$ to output $s_1$) with a phase shift of $180°$,
- $\theta=180°$ corresponds to a direct connection with a phase shift of $90°$,
- $\theta=180°$ corresponds to a cross connection with zero (or $360°$) phase shift.

This rounding approach to discrete values for universal hybrids very much simplifies manufacturing of the compact distributor characterised by the matrix H.

Therefore such a production with a single type of coupler results from the production of a compact control matrix with parameter $\theta$, discretisation of the parameter $\theta$ and the rounding approach to discrete values of $\theta$.

The solutions space can also be discretised at a spacing of $15°$. This, on the other hand, would require two other "branch-line" couplers, one at 3 dB and the other at 11.7 dB. A $30°$ discretisation is sufficient in practice.

With rounding of universal hybrid angles to discrete values at a spacing of $30°$ (or $15°$), a second optimisation has to be carried out on the phase shift matrices $\Phi_k$. The optimisation uses the same routines $f_p$, $f_{nl}$, $f_{lln}$, but the angles of the couplers $\theta_{k,i}$ are then imposed (rounded values).

Figure 5:
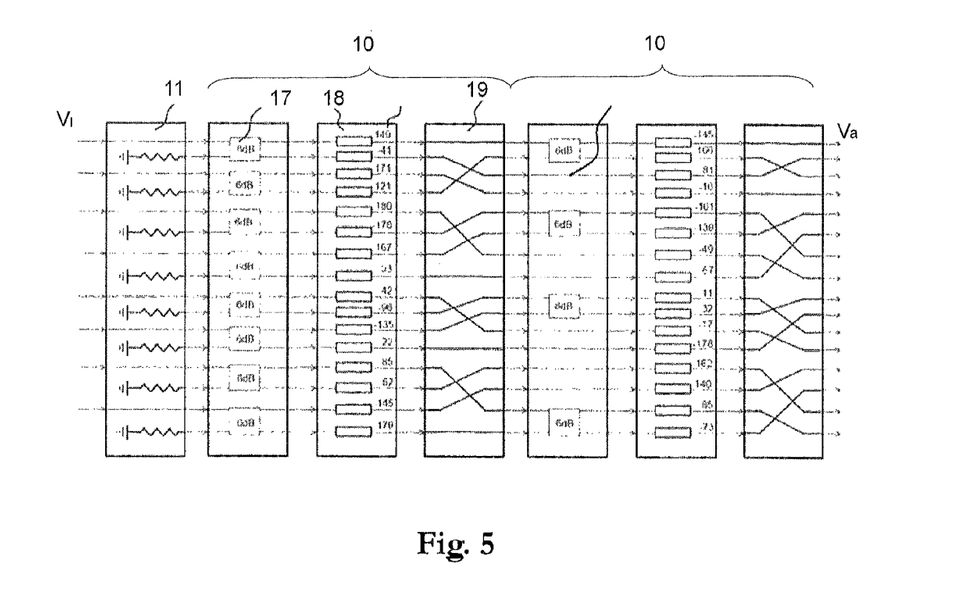
FIG. 5 shows an example two-stage implementation of the reduced matrix H for control of a high frequency antenna of the phased array type.

FIG. 5 shows an example embodiment of a compact distributor associated with the matrix H for controlling an antenna comprising 16 radiating elements from 8 control elements and from the decomposition of a Butler matrix.

The Butler matrix for an antenna with 16 radiating elements usually requires 4 coupler stages. With the method according to the invention, for 8 modes we obtain an approximate result for the Butler matrix with only 2 coupler stages 10, that is sufficiently precise for the MRI application.

Figure 6:
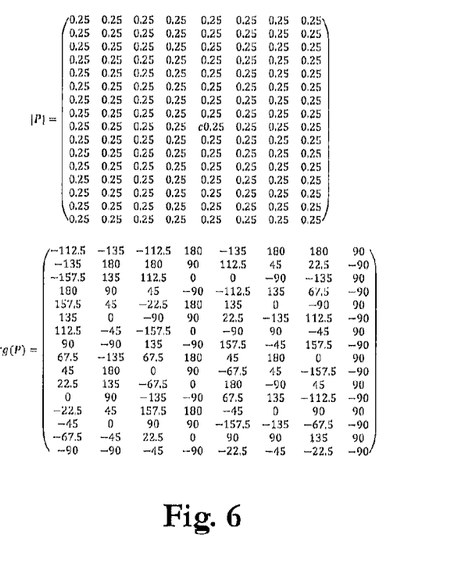
FIG. 6 shows matrices of amplitudes and phases of the Butler matrix for controlling an antenna comprising 16 radiating elements using 8 control elements.

Thus, for the 7 modes circularly polarised along the direction of the spin rotation, and for the MRI application and for mixed mode, the control matrix P with complex values is defined by the amplitude and phase matrices shown in FIG. 6.

The value 0.25 corresponds to $1/\sqrt{16}$ of the input power because each radiating element is powered with the same power. Only the first 4 of the 8 modes are predominant in the homogenisation of spin excitation.

The matrix W was chosen to optimise this embodiment with the following coefficients:

$$W(i,i) = \frac{1}{i+1}.$$

This can give a smaller approximation error for the first modes at the detriment of the last modes. The first optimisation (without rounding) gives a result with the following errors:

$$|P - \tilde{P}| = \begin{pmatrix} 0,04 & 0,04 & 0,07 & 0,05 & 0,04 & 0,13 & 0,22 & 0,26 \\ 0,03 & 0,02 & 0,04 & 0,04 & 0,04 & 0,08 & 0,14 & 0,20 \\ 0,02 & 0,03 & 0,05 & 0,04 & 0,02 & 0,07 & 0,14 & 0,20 \\ 0,04 & 0,04 & 0,07 & 0,05 & 0,02 & 0,11 & 0,20 & 0,24 \\ 0,04 & 0,04 & 0,07 & 0,05 & 0,04 & 0,13 & 0,22 & 0,26 \\ 0,03 & 0,02 & 0,04 & 0,04 & 0,04 & 0,08 & 0,14 & 0,20 \\ 0,02 & 0,03 & 0,05 & 0,04 & 0,02 & 0,07 & 0,14 & 0,20 \\ 0,04 & 0,04 & 0,07 & 0,05 & 0,02 & 0,11 & 0,20 & 0,24 \\ 0,04 & 0,04 & 0,07 & 0,04 & 0,04 & 0,13 & 0,21 & 0,26 \\ 0,02 & 0,02 & 0,04 & 0,03 & 0,03 & 0,08 & 0,15 & 0,21 \\ 0,03 & 0,02 & 0,05 & 0,04 & 0,02 & 0,07 & 0,14 & 0,21 \\ 0,04 & 0,04 & 0,07 & 0,04 & 0,03 & 0,12 & 0,20 & 0,25 \\ 0,04 & 0,04 & 0,07 & 0,05 & 0,02 & 0,11 & 0,20 & 0,24 \\ 0,03 & 0,03 & 0,05 & 0,04 & 0,02 & 0,07 & 0,14 & 0,20 \\ 0,02 & 0,02 & 0,04 & 0,03 & 0,04 & 0,08 & 0,14 & 0,20 \\ 0,04 & 0,04 & 0,07 & 0,05 & 0,04 & 0,13 & 0,22 & 0,26 \end{pmatrix}$$

This result shows that effectively, the error is greater for the last modes (last columns in the error matrix), for which the values of W were smaller.

After rounding to a discrete solution space at $30°$, the second optimisation produces a solution characterised by the following error matrix:

$$|P - \tilde{P}| = \begin{pmatrix} 0,06 & 0,01 & 0,02 & 0,05 & 0,04 & 0,11 & 0,22 & 0,22 \\ 0,07 & 0,04 & 0,04 & 0,07 & 0,04 & 0,11 & 0,22 & 0,27 \\ 0,03 & 0,03 & 0,05 & 0,05 & 0,02 & 0,08 & 0,22 & 0,26 \\ 0,03 & 0,01 & 0,03 & 0,03 & 0,02 & 0,07 & 0,16 & 0,17 \\ 0,06 & 0,01 & 0,02 & 0,05 & 0,04 & 0,11 & 0,22 & 0,22 \\ 0,07 & 0,04 & 0,04 & 0,07 & 0,04 & 0,11 & 0,22 & 0,27 \\ 0,03 & 0,03 & 0,05 & 0,05 & 0,02 & 0,08 & 0,22 & 0,26 \\ 0,03 & 0,01 & 0,03 & 0,03 & 0,02 & 0,07 & 0,16 & 0,17 \\ 0,06 & 0,01 & 0,02 & 0,05 & 0,04 & 0,11 & 0,22 & 0,22 \\ 0,07 & 0,04 & 0,04 & 0,07 & 0,03 & 0,11 & 0,22 & 0,27 \\ 0,03 & 0,03 & 0,05 & 0,05 & 0,02 & 0,08 & 0,22 & 0,26 \\ 0,03 & 0,01 & 0,03 & 0,03 & 0,03 & 0,07 & 0,16 & 0,17 \\ 0,03 & 0,01 & 0,03 & 0,03 & 0,02 & 0,07 & 0,16 & 0,17 \\ 0,03 & 0,03 & 0,05 & 0,05 & 0,02 & 0,08 & 0,22 & 0,26 \\ 0,07 & 0,04 & 0,04 & 0,07 & 0,04 & 0,11 & 0,22 & 0,27 \\ 0,06 & 0,01 & 0,02 & 0,05 & 0,04 & 0,11 & 0,22 & 0,22 \end{pmatrix}$$

It can be seen that the reduction in the implementation to a single 6 dB "branch-line" type coupler does not significantly increase synthesis errors but it does very much simplify the hardware production of the compact distributor shown in FIG. 5.

Figure 7A:
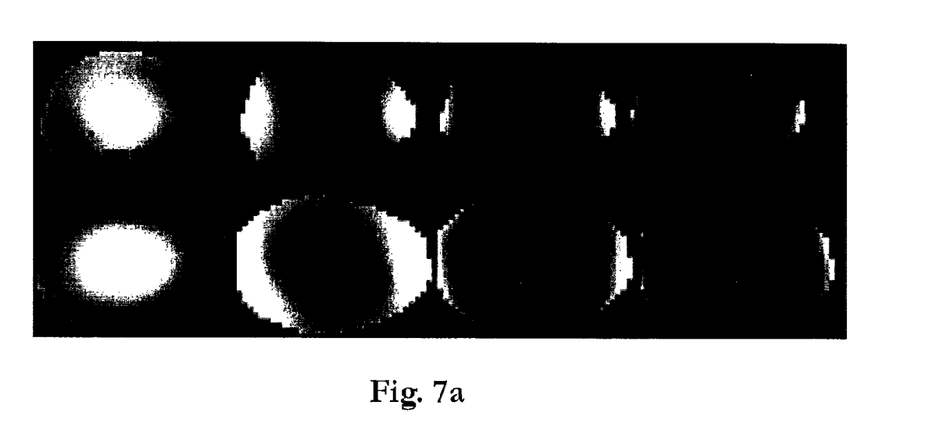
FIG. 7a shows field maps for odd modes 1, 3, 5 and 7 obtained using a Butler matrix.
Figure 7B:
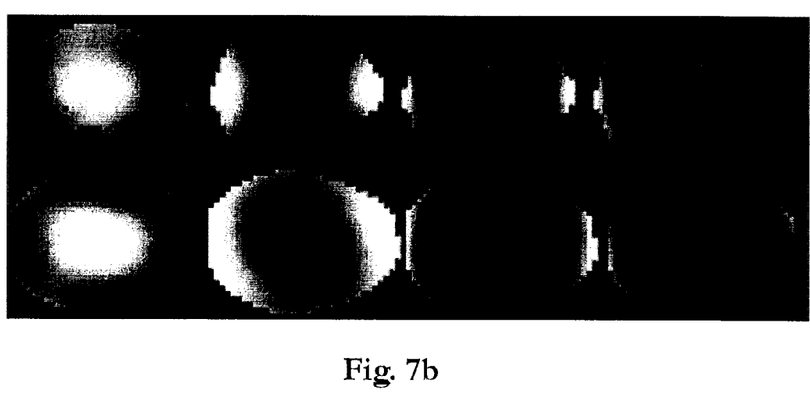
FIG. 7b shows field maps for odd modes 1, 3, 5 and 7 obtained using the control module implemented by the method according to the invention.

FIGS. 7a and 7b show field maps obtained for modes 1, 3, 5 and 7 for sagittal and axial sections of a model brain, to give an idea of the precision of the synthesis of control modes on so-called field maps |B1+| used for excitation of spins in MRI obtained by the method according to the invention in comparison with a method using only the Butler matrix for implementation of the control module. FIG. 7a shows field maps obtained with the original Butler matrix (i.e. 4 stages) and FIG. 7b shows field maps obtained using the control module according to the invention comprising two stages.

The invention claimed is:

1. Method of making a compact control module of a high frequency antenna for a magnetic resonance imaging device comprising a plurality M of control elements and a plurality N of radiating elements, said plurality N of radiating elements being greater than said plurality M of control elements, said control module being represented by a control matrix $\tilde{P}$, where $\tilde{P}$ is a matrix approximately equal to a control matrix P to control said plurality N of radiating elements using said plurality M of control elements; said method comprising:

decomposing the approximate control matrix $\tilde{P}$ into a product of two matrices H×L; the first matrix L with dimensions M×M being capable of transforming a plurality M of signals $V_m$ transmitted by said plurality M of control elements into M signals $V_l$, in amplitude and in phase; the second matrix H with dimensions N×M receiving said M signals $V_l$, as inputs;

producing said matrix H with a number of stages less than a number of stages necessary for implementation of the control matrix P, said stages being implemented by coupling means, phase shifting means and permutation means;

using said matrix L by software means starting from implementation of said matrix H determined during the producing.

2. Method of making a control module of a high frequency antenna for a magnetic resonance imaging device according to claim 1, wherein said implemented matrix H comprises a number of stages K less than:

$E_{sup}(\ln(N)/\ln(2))$, where $E_{sup}$ corresponds to the next higher integer part
N corresponds to the number of radiating elements of the antenna;
"ln" corresponds to the Naperian logarithm.

3. Method of making a control module of a high frequency antenna for a magnetic resonance imaging device according to claim 1, comprising decomposing the matrix H into a plurality K+1 of matrices S according to the following relation:

$H = S_K, S_{K-1}, \ldots, S_1 S_0$ where: $S_0$ is a matrix with dimensions N×M
$S_k$ is a matrix with dimensions N×N where $k = \{1, \ldots, K\}$.

4. Method of making a control module of a high frequency antenna for a magnetic resonance imaging device according to claim 3, wherein each of said matrices $S_k$ where $k = \{1, \ldots, K\}$ is formed by the matrix product of a coupling matrix $C_k$, a phase shift matrix $\Phi_k$ and a permutation matrix $\Pi_k$ such that a signal $X_{k+1}$ at the output from stage k of the control module depends on the relation:

$X_{k+1} = S_k X_k = \Pi_k \Phi_k C_k X_k$, where $X_k$ represents the input signal to said stage k.

5. Method of making a control module of a high frequency antenna for a magnetic resonance imaging device according to claim 4, wherein said coupling matrix $C_k$ is implemented by said coupling means, said phase shift matrix $\Phi_k$ is implemented by said phase shift means, and said permutation matrix $\Pi_k$ is implemented by said permutation means.

6. Method of making a control module of a high frequency antenna for a magnetic resonance imaging device according to claim 5, wherein said coupling means are universal hybrid couplers.

7. Method of making a control module of a high frequency antenna for a magnetic resonance imaging device according to claim 5, wherein said coupling means are universal 6 dB hybrid couplers.

8. Control module obtained by the manufacturing method according to claim 1, comprising an arrangement of coupling means, phase shift means and permutation means and software means such that said N signals $V_a$ output from said control module depend on the relation:

$V_a = HLV_m$ where
$V_m$ represents the M input signals to said control module;
H is the matrix with dimensions N×M that can be implemented by said coupling means, said phase shift means and said permutation means;
L is the matrix with dimensions M×M that can be used by said software means.

* * * * *

UNITED STATES PATENT AND TRADEMARK OFFICE
CERTIFICATE OF CORRECTION

PATENT NO. : 9,562,957 B2  
APPLICATION NO. : 14/233936  
DATED : February 7, 2017  
INVENTOR(S) : Guillaume Ferrand et al.

Page 1 of 1

It is certified that error appears in the above-identified patent and that said Letters Patent is hereby corrected as shown below:

On the Title Page

Item (57) Abstract:
Please correct Line 12 of the Abstract as follows:
"...producing the matrix H with a number of stages less than..."

Signed and Sealed this
Ninth Day of May, 2017

Michelle K. Lee
*Director of the United States Patent and Trademark Office*